(12) United States Patent
Yamaguchi et al.

(10) Patent No.: US 7,925,461 B2
(45) Date of Patent: Apr. 12, 2011

(54) QUALITY CONTROL SYSTEM, ANALYZER, AND QUALITY CONTROL METHOD

(75) Inventors: Tadayuki Yamaguchi, Kobe (JP); Atsushi Shirakami, Miki (JP); Etsuro Shinkai, Kobe (JP); Yasuhiro Ochi, Miki (JP)

(73) Assignee: Sysmex Corporation, Kobe (JP)

( * ) Notice: Subject to any disclaimer, the term of this patent is extended or adjusted under 35 U.S.C. 154(b) by 329 days.

(21) Appl. No.: 11/903,364

(22) Filed: Sep. 21, 2007

(65) Prior Publication Data

US 2008/0114559 A1 May 15, 2008

(51) Int. Cl.
*G06F 19/00* (2011.01)
(52) U.S. Cl. ........... 702/84; 702/22; 702/81; 702/82; 702/83; 702/187; 700/109; 700/110
(58) Field of Classification Search ............ 702/22, 702/81–84, 187; 700/109–110
See application file for complete search history.

(56) References Cited

U.S. PATENT DOCUMENTS

| 5,835,384 | A | 11/1998 | Lin |
| 6,937,964 | B2 | 8/2005 | Okuno et al. |
| 2004/0220761 | A1* | 11/2004 | Yundt-Pacheco .......... 702/84 |
| 2005/0177345 | A1 | 8/2005 | Okuno et al. |
| 2007/0217949 | A1* | 9/2007 | Mimura et al. .......... 422/63 |

FOREIGN PATENT DOCUMENTS

JP 2004-20323 1/2004

OTHER PUBLICATIONS

European Search Report for Application No. 07018258.9 dated May 19, 2009.
de Graeve, J.S.; Cambus, J.P.; Gruson, A.; Valdiguié, P.M. "Automated Technical Validation—a Real Time Expert System for Decision Support," *Clinica Chimica Acta*, 1996, 248, 39-49.
McDowall, R.D.; Pearce, J.C.; Murkitt, G.S. "Laboratory Information Management Systems—Part I. Concepts," *Journal of Pharmaceutical & Biomedical Analysis*, 1988, 6, 339-359.

* cited by examiner

*Primary Examiner* — Sujoy K Kundu
(74) *Attorney, Agent, or Firm* — Brinks Hofer Gilson & Lione

(57) ABSTRACT

A quality control method using a plurality of analyzers and a control device connected to the analyzers via a network, the method comprising: (a) measuring quality control samples by the analyzers; (b) collecting a plurality of quality control data obtained by measuring the quality control samples; (c) implementing a quality control by the control device based on the collected quality control data; (d) obtaining uncertainty of measurement of analyzer based on uncertainty of analyzer calibration and the quality control data; (e) outputting a result of the quality control; and (f) outputting the uncertainty of measurement is disclosed. A quality control system and an analyzer are also disclosed.

11 Claims, 8 Drawing Sheets

QUALITY CONTROL SYSTEM, ANALYZER, AND QUALITY CONTROL METHOD

RELATED APPLICATIONS

This application claims priority under 35 U.S.C. §119 to Japanese Patent Application No. 2006-256702 filed Sep. 22, 2006, the entire content of which is hereby incorporated by reference.

FIELD OF THE INVENTION

The present invention relates to a quality control system, analyzer, and quality control method, and specifically relates to an analyzer, quality control method, and a quality control system provided with a plurality of analyzers and a quality control apparatus connected over a network to the plurality of analyzers.

BACKGROUND

There is a need to ascertain the uncertainty of measurement data obtained by analyzers. For example, Japanese Laid-Open Patent Publication No. 2004-20323 discloses a measuring device that calculates the composite uncertainty by combining the uncertainty of the allowable margin of error of devices of the measurement unit, the uncertainty of device operation, the uncertainty of the calibration curve when measuring a standard sample, and the uncertainty of the measurement values of unknown samples when such unknown samples are measured.

Quality control systems are known which collect the measurement data of quality control substances using a network, and perform quality control based on collected measurement data (for example, U.S. Pat. No. 6,937,964). This quality control system is capable of comparing measurement data of quality control substances from analyzers at the same facility, and measurement data of quality control substances from analyzers at other facilities. Therefore, an operator of an analyzer connected to this quality control system compares the measurement data from the same facility with average values or the like of measurement data from other facilities, and determines that a sample can be measured by the analyzer when the collected measurement data are within an allowed range.

Japanese Laid-Open Patent Publication No. 2004-20323 does not disclose, however, a method for evaluating a measurement apparatus by the composite uncertainty of measurement data combined by the measurement apparatus. Therefore, the operator of the analyzer can not determine whether or not a sample can be measured by the analyzer based on uncertain data even when the measurement apparatus has calculated the uncertainty of the measurement data. The measurement apparatus disclosed in Japanese Laid-Open Patent Publication No. 2004-20323 must perform multiple measurements of the same unknown sample in order to calculate the uncertainty of the measurement values of the unknown sample when an unknown sample is measured. Since samples are usually collected from a patient, however, collecting sufficient unknown sample from a patient for several measurements places a burden on the patient.

Furthermore, although the quality control system disclosed in U.S. Pat. No. 6,937,964 is extremely useful, including uncertainty in the measurement data was not considered.

SUMMARY

The scope of the present invention is defined solely by the appended claims, and is not affected to any degree by the statements within this summary.

A first aspect of the present invention is a quality control system comprising a plurality of analyzers and a control device connected to the analyzers via a network, the quality control system comprising: measurement units for measuring samples, the measurement units being provided in each of the analyzers; quality control data transmitting means for transmitting, to the control device via the network, quality control data obtained by the measurement units by measuring quality control samples, the quality control data transmitting means being provided in each of the analyzers; quality control data receiving means for receiving a plurality of quality control data sent from each of the quality control data transmitting means, the quality control data receiving means being provided in the control device; quality control means for implementing quality control based on the quality control data received by the quality control data receiving means, the quality control means being provided in the control device; calibration uncertainty memory for storing uncertainty of analyzer calibration for each of the analyzers; measurement uncertainty obtaining means for obtaining uncertainty of measurement of analyzer based on the uncertainty of analyzer calibration and the quality control data; quality control result output means for outputting a result of quality control obtained by the quality control means; and measurement uncertainty output means for outputting the uncertainty of measurement obtained by the measurement uncertainty obtaining means.

A second aspect of the present invention is an analyzer connected, via a network, to a control device which is connected to a plurality of analyzers via the network, receives a plurality of quality control data obtained by measuring quality control samples by the analyzers, implements quality control based on the received quality control data, and transmits a result of the quality control to each of the analyzers, the analyzer comprising: a measurement unit for measuring samples; quality control data transmitting means for transmitting quality control data obtained by measuring a quality control sample by the measurement unit to the control device via the network; receiving means for receiving the result of the quality control sent from the control device; calibration uncertainty memory for storing uncertainty of analyzer calibration; measurement uncertainty obtaining means for obtaining uncertainty of measurement of analyzer based on the uncertainty of analyzer calibration and the quality control data; quality control result output means for outputting the result of the quality control; and measurement uncertainty output means for outputting the uncertainty of measurement.

A third aspect of the present invention is an analyzer comprising: a measurement unit for measuring samples; calibration uncertainty memory for storing uncertainty of analyzer calibration; measurement uncertainty obtaining means for obtaining uncertainty of measurement of analyzer based on the uncertainty of analyzer calibration and quality control data obtained by measuring a quality control sample by the measurement unit; and measurement uncertainty output means for outputting the uncertainty of measurement.

A fourth aspect of the present invention is a quality control method using a plurality of analyzers and a control device connected to the analyzers via a network, the method comprising: (a) measuring quality control samples by the analyzers; (b) collecting a plurality of quality control data obtained by measuring the quality control samples; (c) implementing a quality control by the control device based on the collected quality control data; (d) obtaining uncertainty of measurement of analyzer based on uncertainty of analyzer calibration and the quality control data; (e) outputting a result of the quality control; and (f) outputting the uncertainty of measurement.

A fifth aspect of the present invention is a quality control method using an analyzer connected, via a network, to a control device which is connected to a plurality of analyzers via the network, receives a plurality of quality control data obtained by measuring quality control samples by the analyzers, implements quality control based on the received quality control data, and transmits a result of the quality control to each of the analyzer, the method comprising: (a) measuring a quality control sample by the analyzer; (b) transmitting quality control data obtained by measuring the quality control sample from the analyzer to the control device via the network; (c) obtaining uncertainty of measurement of analyzer based on uncertainty of analyzer calibration and the quality control data; and (d) outputting the uncertainty of measurement.

A sixth aspect of the present invention is a quality control method for an analyzer, the method comprising: (a) measuring a quality control sample; (b) obtaining uncertainty of measurement of analyzer based on uncertainty of analyzer calibration and quality control data obtained by measuring the quality control sample; and (c) outputting the uncertainty of measurement.

DETAILED DESCRIPTION OF THE PREFERRED EMBODIMENTS

The preferred embodiments of the present invention are described hereinafter with reference to the drawings.

Figure 1:
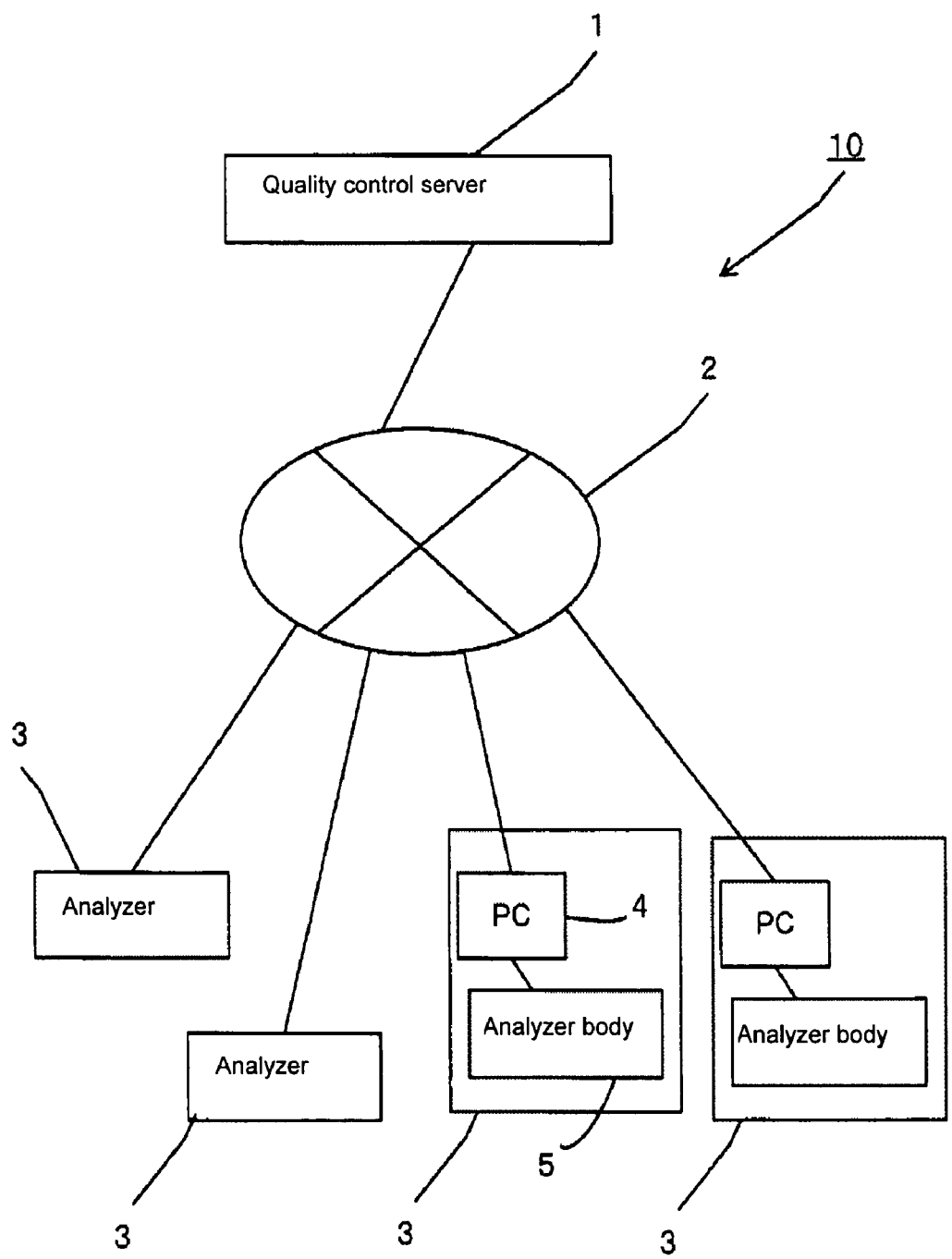
FIG. 1 is a network structural diagram of a quality control system.

As shown in FIG. 1, the embodiment of the quality control system 10 is provided with a quality control server 11, and a plurality of analyzers 3 which are connected to the quality control server 11 via a network such as the internet or the like. Sample analyzers such as biological analyzers, hemocytometers, blood coagulation analyzers, immunoanalyzers, urine analyzers and the like may be used as the analyzer 3. The analyzer 3, which is connected to the quality control server 1, is not limited to a single type inasmuch as a plurality of types of apparatus such as biological analyzers and hemocytometers and the like may be used. To simplify the following description, however, an example is used in which only hemocytometers are connected. An analyzer which functions as the analyzer in a configuration in which an analyzer 5 and a data processing device 4 are connected may be used as the analyzer 3, and an analyzer which incorporates an input device, display, and controller and the like in an analyzer body 3 may be used as the analyzer 3.

The quality control server 1 may be installed at the manufacturer-seller which manufactures and sells the analyzer 3, or installed at a leaser installation. The analyzers 3 are installed at a plurality of laboratory facilities. The quality control server 1 performs external quality control based on quality control data sent from a plurality of facilities via a network 2. The external quality control process is accomplished by the quality control server 1 performing statistical processing of quality control data (internal quality control data) received from the analyzers 3 which measure quality control samples (also referred to as control substances) in each of the facilities.

Furthermore, the quality control server 1 calculates the uncertainty of measurement of the analyzers 3.

Figure 2:
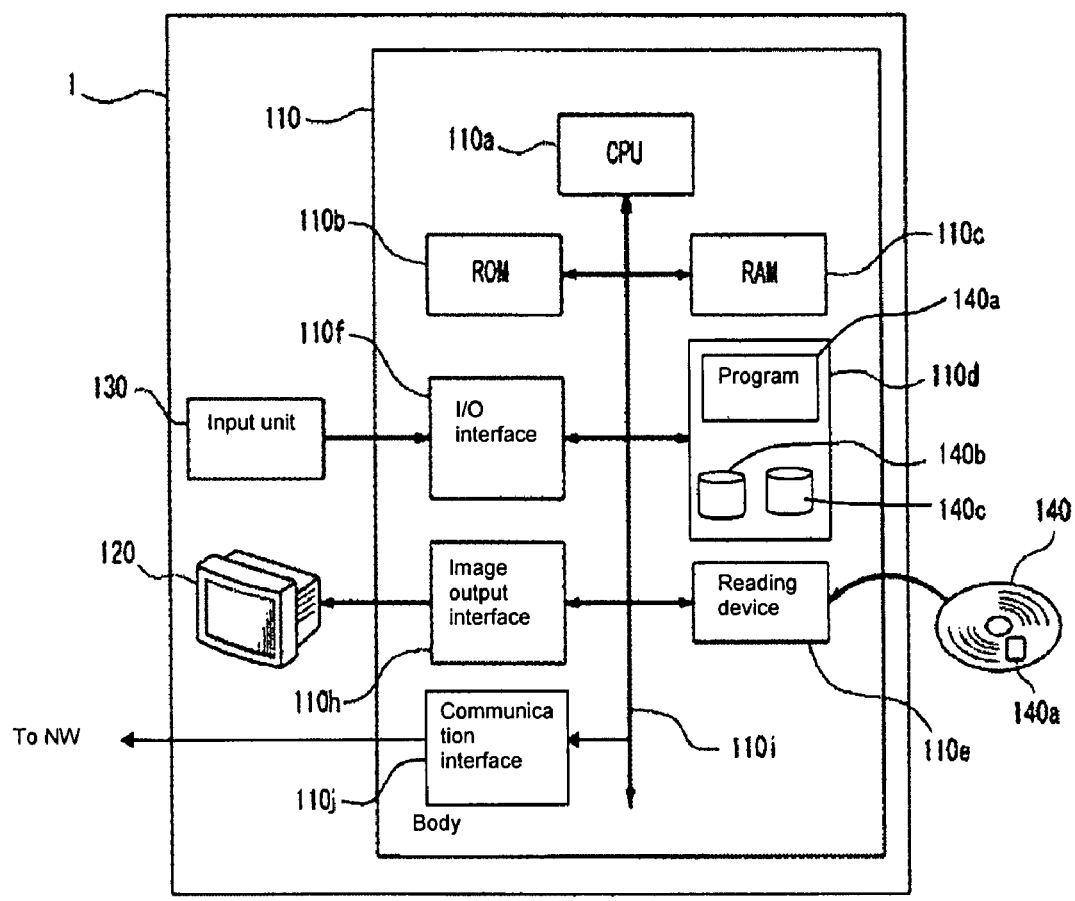
FIG. 2 is a hardware structural diagram of the quality control server.

FIG. 2 is a block diagram showing the hardware structure of the server 1. The server 1 is a computer mainly configured by a body 110, a display 120, and an input device 130.

The body 110 is mainly configured by a CPU 110a, ROM 110b, RAM 110c, hard disk 110d, reading device 110e, input/output interface 110f, image output interface 110h, and communication interface 110j, and the CPU 110a, ROM 110b, RAM 110c, hard disk 110d, reading device 110e, input interface 110f, image output interface 110h, and communication interface 110j are connected via a bus 110i so as to be capable of communication.

The CPU 110a is capable of executing computer programs stored in the ROM 110b, and computer programs loaded in the RAM 110cc. The computer functions as the server 1 when the CPU 110a executes an application program 140a to realize each of the function blocks as described later.

The ROM 110b is configured by a mask ROM, PROM, EPROM, EEPROM or the like, and stores computer programs executed by the CPU 110a and data and the like used in conjunction therewith.

The RAM 110c is configured by SRAM, DRAM or the like. The RAM 110c is used when reading the computer program recorded in the ROM 110b and on the hard drive 110d. The RAM 110c is further used as a work area of the CPU 110a when these computer programs are being executed.

The hard drive 110d contains various installed computer programs to be executed by the CPU 110a such as an operating system and application programs and the like, as well as data used in the execution of these computer programs. The application program 140a is also installed on the hard disk 110d.

The reading device 110e is configured by a floppy disk drive, CD-ROM drive, DVD-ROM drive or the like, and is capable of reading the computer programs and data stored on a portable recording medium 140. Furthermore, the portable recording medium 140 may also store the application program 140a which allows the computer to function as the system of the present invention, such that the computer is capable of reading the application program 140a from the portable recording medium 140 and installing the application program 140a on the hard disk 110d.

The application program 140a can be provided not only by the portable recording medium 140, it also may be provided from an external device connected to the computer so as to be capable of communication over an electric communication line by means of this electric communication line (wire line or wireless). For example, the application program 140a may be stored on the hard disk of a server computer connected to the internet, such that the computer can access the server computer and download the application program 140a, and then install the application program 140a on the hard disk 110d.

Also installed on the hard disk 110d is an operating system providing a graphical user interface, such as, for example, Windows (registered trademark) of Microsoft Corporation, U.S.A. In the following description, the application program 140a of the present embodiment operates on such an operating system.

Furthermore, predetermined regions of the hard disk 110d are used as a quality control data DB (database) 140b for storing quality control data received from the analyzers 3, and a calibration uncertainty DB (database) 140c for storing uncertainty of calibration which is described later.

The I/O interface 110f is configured by a serial interface such as a USB, IEEE1394, RS232C or the like, parallel interface such as SCSI, IDE, IEEE1284 or the like, analog interface such as a D/A converter, A/D converter or the like. The input device 130, which is configured by a keyboard and mouse, is connected to the input/output interface 110f, such that an operator can input data to the computer 100a using the input device 130.

The communication interface 110j is, for example, an Ethernet (registered trademark) interface, such that the server 1 can send and receive data to and from the analyzers 3 which are connected via the network 2 using a predetermined communication protocol using the communication interface 110j.

The image output interface 110h is connected to the display 120 which is configured by configured by an LCD, CRT or the like, such that image signals corresponding to the image data received from the CPU 110a can be output to the display 120. The display 120 displays an image (screen) in accordance with the input image signals.

Figure 3:
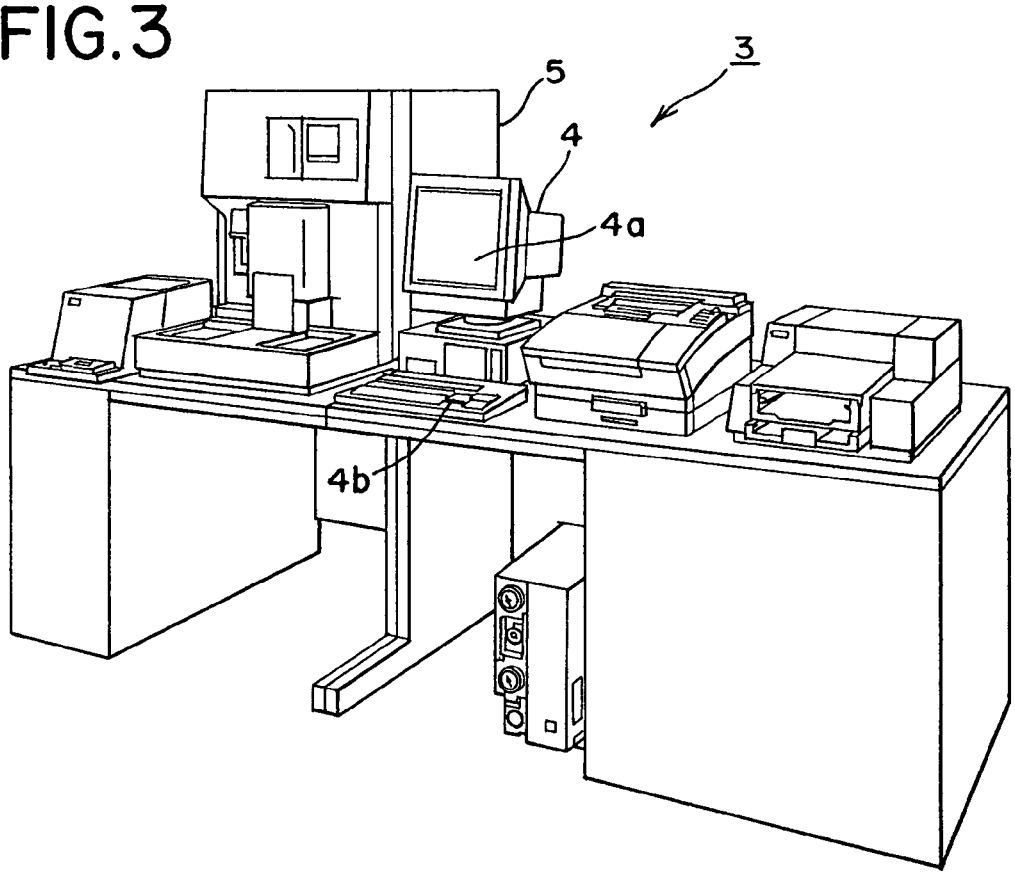
FIG. 3 is a perspective view showing a structural overview of an analyzer 3.

FIG. 3 is a perspective view showing a structural overview of an analyzer 3. FIG. 3 is a perspective view showing the external structures of the hemocytometer 5 and data processing device 4. The analyzer 3 is a hemocytometer which uses blood samples, and is configured so as to be capable of classifying and counting the blood cells contained in blood samples. The data processing device 4 is provided with a display 4a and a keyboard 4b, and is configured so as to be capable of data input and display.

Figure 4:
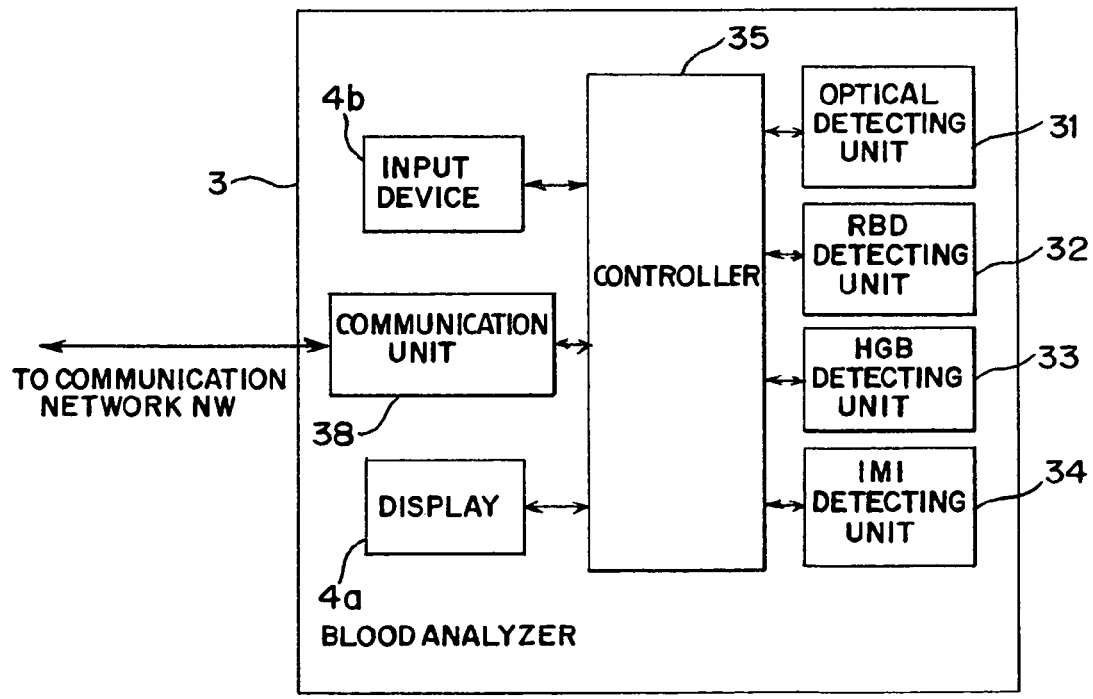
FIG. 4 is a block diagram showing the structure of the analyzer 3.

FIG. 4 is a block diagram showing the structure of the analyzer 3. The analyzer 3 has an optical detecting unit 31, RBC detecting unit 32, HGB detecting unit 33, IMI detecting unit 34, controller 35, and communication interface 38 as main structural elements. The controller 35 is configured by a CPU, ROM, RAM and the like, so as to control the operation of each of the structural elements of the analyzer 3. The communication interface 38 is, for example, an Ethernet (registered trademark) interface, which allows data to be sent and receive to/from the server 1. The controller 35 and the communication interface 38 are provided in the data processing device 4, such that the data received from the server 1 via the communication interface 38 can be displayed on the display 4a when the controller 35 performs specific controls. The display 4a and the keyboard 4b are connected to the controller 35 such that data input and display are controlled by the controller 35.

The optical detecting unit 31 is capable of measuring white blood cells, nucleated red blood cells, and reticulocytes using flow cytometry that employs a semiconductor laser. The RBC detecting unit 32 is capable of measuring red blood cells and platelets using sheath flow-DC detection. The HGB detecting unit 33 is capable of measuring hemoglobin (HGB) using an SLS hemoglobin method. The IMI detecting unit 34 is capable of measuring the frequency of immature erythrocytes in a sample using an RF/DC detection method.

The quality control process performed by the quality control system 10 is described below using FIG. 5. The figure shows the relationship between the server 1 and a single analyzer 3 to simplify the description, while the server 1 actually runs parallel quality control processes for a plurality of analyzer 3. This analyzer 3 is referred to as analyzer A in the following description.

The quality control process on the analyzer side shown on the left side of the figure may start when the analyzer A reads a barcode representing the control substance by a barcode reader which is not shown in the figure, or may start when the operator of the analyzer A issues an instruction to measure a control substance using the keyboard 4b.

The quality control process on the quality control server 1 side, however, may be executed whenever required after the server 1 has started.

When the analyzer A reads the barcode representing the control substance, the analyzer A first measures the control substance in step S1. Then, in step S2, the quality control data, which include the measurement result of the control substance, are sent to the server 1. Specifically, the quality control data include measurement values such as the red cell count, white cell count, hemoglobin level, and hematocrit value and the like obtained by measuring the control substance, control substance lot number, day and time at which the control substance was measured, and analyzer ID identifying analyzer A. The quality control data may be the quality control data obtained by a single measurement of the control substance, or may be average value of a plurality of measurement data obtained by a plurality of measurements of the same control substance. Steps S1 and S2 may also determine whether or not a sample is a control substance from the barcode when the analyzer A reads the barcode adhered to a sample container, and may send the quality control data to the server 1 when the sample is a control substance, and not send the measurement data to the server 1 when the sample is a patient sample.

The server awaits the transmission of the quality control data, and when such quality control data are sent the server 1 receives the quality control data in step S11 via the communication interface 110j. When the server 1 receives the quality control data (step S11:YES), the received quality control data are associated with the analyzer ID and measurement date and time of the control substance and stored in the quality control DB 140b.

The plurality of quality control data, which have been sent from a plurality of analyzers 3 including the analyzer A, is sorted for each analyzer and stored whenever required.

The server 1 performs the quality control process in step S13. The quality control process is performed by statistically processing the quality control data sent from all the analyzers 3 to the server 1 within a predetermined period (for example, within one month).

In the quality control process (step S13), the server 1 calculates the SDI value representing the quality control information among facilities (among analyzers).

More specifically, the SDI represents the degree of deviation between the quality control data obtained by the analyzer A and the average value of the quality control data obtained within the predetermined period by all analyzers 3 connected to the server 1, and the SDI calculation is accomplished using equation (3) below.

$$SDI = \{(\text{quality control data obtained by analyzer A}) - (\text{average value of quality control data sent within}}$$

a predetermined time from all analyzers 3 connected to the server 1}$\sqrt{\{\overline{1}(m-1)\Sigma(i=1 \text{ to } m)ni (ai-b)^2\}}$ (3)

In this case, m represents the number of analyzers connected to the server 1, ni represents the number of quality control data of each analyzer within a predetermined time, ai represents the average value of the control data of each analyzer within a predetermined time, and b represents the average value of the quality control data of the plurality of analyzers within a predetermined time.

In the quality control process (step S13), the server 1 also calculates the PI value which represents quality control information within an installation (within the analyzer).

More specifically, the PI represents the ratio of divergence between the quality control data obtained by the analyzer A and the divergence of the quality control data obtained within the predetermined period by all analyzers 3 connected to the server 1, and the PI calculation is accomplished using equation (4) below.

PI=(standard deviation of quality control data obtained by analyzer A within a predetermined period)/$\sqrt{\{1(N-m)\Sigma(i=1 \text{ to } m)(ni-1)Si^2\}}$ (4)

In this case, N represents the number of quality control data sent to the server 1 within a predetermined period, m represents the number of analyzers connected to the server 1, ni represents the number of quality control data of each analyzer within a predetermined time, and Si represents the standard deviation of the quality control data of each analyzer within a predetermined time.

Figure 6:
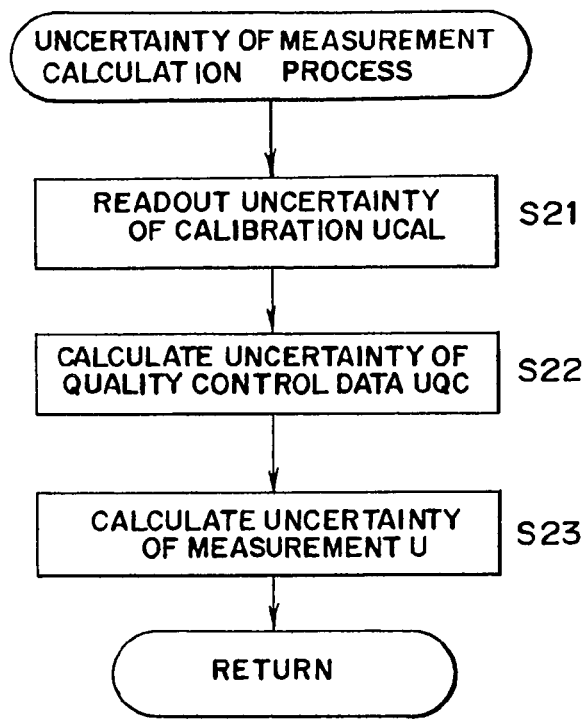
FIG. 6 is a flow chart of the uncertainty of measurement calculation.

Next, in step S14, the server 1 calculates the uncertainty of measurement of a normal examination by the analyzer A. In this process, the uncertainty of calibration $u_{CAL}$ of the analyzer A is first read from the calibration uncertainty DB 140c, as shown in FIG. 6 (step S21).

The uncertainty of calibration $u_{CAL}$ of the analyzer A is obtained beforehand by the manager of the server 1 and stored in the calibration uncertainty DB 140c. The method of obtaining the uncertainty of calibration $u_{CAL}$ is described below using FIG. 7.

Figure 7:
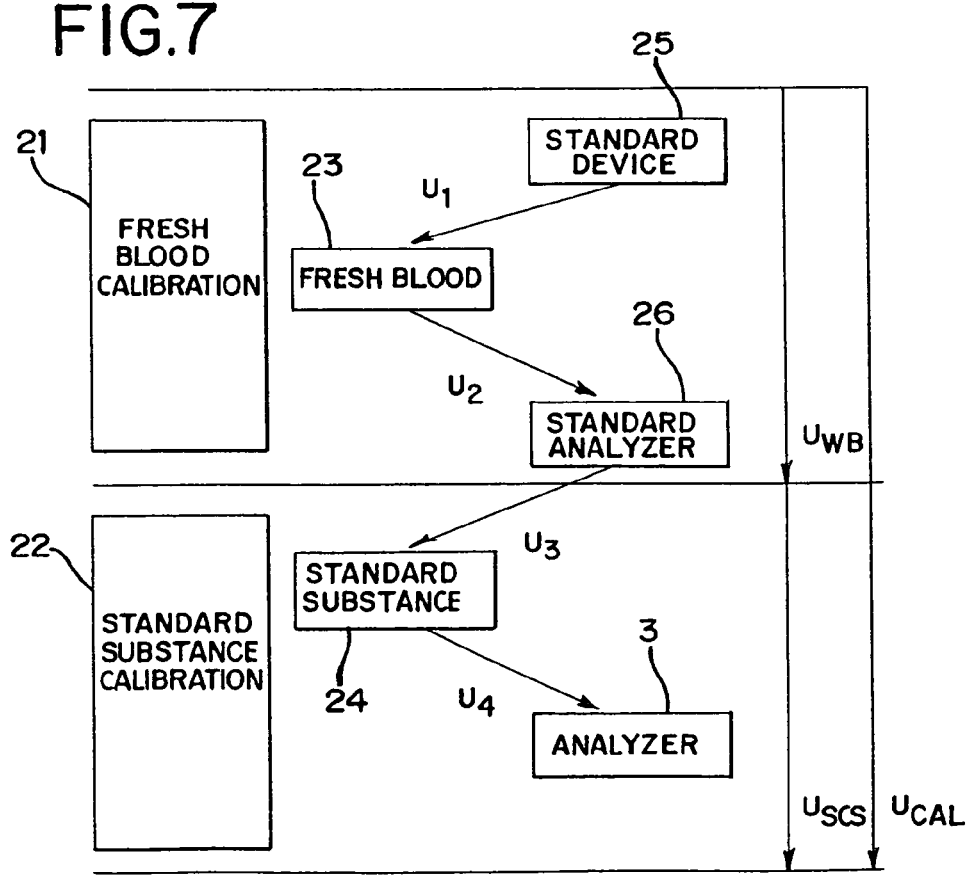
FIG. 7 is a conceptual view of the method for calculating the uncertainty of calibration.

As shown in FIG. 7, the uncertainty of calibration data $u_{CAL}$ is calculated by combining the uncertainty of calibration data $u_{WB}$ of fresh blood 23, and the uncertainty of calibration data $u_{SCS}$ of a standard substance 24. The fresh blood 23 is human blood for which the measurement data are unknown. The standard substance 24 is an artificial substance whose measurement data are known, and this substance is used to calibrate the analyzer A. Specifically, the analyzer A is calibrated (adjusted) such that the measurement result of the standard substance 24 obtained by the analyzer A matches the measurement result of the standard substance 24 obtained by a standard analyzer 26.

Obtaining the uncertainty of calibration $u_{CAL}$ is accomplished by a user skilled at operating the analyzer 3 and standard device 25, the user being a technician or the like who normally operated the analyzer 3, for example, a person affiliated with the manufacturer-seller of the analyzer 3. Such a technician measures the fresh blood 23 a predetermined number of times (that is, several times; for example, ten times) using the standard device 25 which conforms to internal standards of measurement. Then, the standard deviation u1 of the obtained plurality of measurement data is calculated. The technician measures the same fresh blood 23 a predetermined number of times (that is, a plurality of times) using the standard analyzer 26 which is used as the standard device of the analyzer A and is the same type of analyzer as the analyzer A. The standard analyzer 26 is calibrated (adjusted) so that the measurement data of the fresh blood 23 matches the measurement data of the fresh blood 23 measured by the standard device 25. Then, the standard deviation $u_2$ of the obtained plurality of measurement data is calculated. Thereafter, the uncertainty of calibration $u_{WB}$ of the fresh blood 23 is calculated by combining $u_1$ and $u_2$. For example, equation (5) below can be used in the calculation of $u_{WB}$.

$$u_{WB} = \sqrt{(u_1^2 + u_2^2)}$$ (5)

The uncertainty of calibration $u_{WB}$ can also be calculated by combining $u_0$, $u_1$, and $u_2$, since the standard device 25 also has an uncertainty u0 caused by the uncertainty of the measuring unit and the like provided in the standard device including the standard device 25. Thus, the uncertainty of calibration $u_{WB}$ is made more accurate.

Next, the technician measures the standard substance 24 a predetermined number of times (that is, a plurality of times) using the standard analyzer 26. Then, the standard deviation u3 of the obtained plurality of measurement data is calculated. The technician departs for the laboratory at which the analyzer A is installed, and measures the same standard substance 24 a predetermined number of times (that is, a plurality of times) using the analyzer A. Then, the standard deviation u4 of the obtained plurality of measurement data is calculated. The uncertainty of calibration $u_{SCS}$ of the standard substance 24 is then calculated by combining $u_3$ and $u_4$. For example, equation (6) below can be used in the calculation of $u_{SCS}$.

$$u_{SCS} = \sqrt{(u_3^2 + u_4^2)}$$ (6)

The uncertainty of calibration $u_{CAL}$ of the analyzer A is then calculated by combining $u_{WB}$ and $u_{SCS}$. Equation (7) below, for example, can be used in the calculation of $u_{CAL}$.

$$u_{CAL} = \sqrt{(u_{WB}^2 + u_{SCS}^2)}$$ (7)

The method of calculating the uncertainty of calibration $u_{CAL}$ of the analyzer A is only an example inasmuch as various other methods may be used.

The uncertainty of calibration $u_{CAL}$ of the analyzer A obtained in this manner is associated with the analyzer ID which identifies the analyzer A, and stored in the calibration uncertainty DB 140c using the input unit 130 or the like. The uncertainty of calibrations $u_{CAL}$ are obtained by this method for all the plurality of analyzers 3 and stored in the calibration uncertainty DB 140c.

The uncertainty of measurement calculation process is described below with reference to FIG. 6. After the server 1 has calculated and read the stored uncertainty of calibration data $u_{CAL}$ from the calibration uncertainty DB 140c, the server 1 calculates the uncertainty of the quality control data $u_{QC}$. For example, the standard deviation of the quality control data of a predetermined past number of times sent from the analyzer A may be used as the uncertainty of the quality control data $u_{QC}$. Each time such data are received, the server 1 stores the quality control data in the quality control DB 140b, and the quality control data of a predetermined past number of times can be read from the quality control DB 140b.

Then, the server 1 calculates the uncertainty of measurement u in a normal examination by combining $u_{CAL}$ and $u_{QC}$ in step S23. Equation (8) below, for example, can be used in the calculation of u.

$$u = \sqrt{(u_{CAL}^2 + u_{QC}^2)}$$ (8)

The term u represents a standard uncertainty of measurement in a normal examination, and the extended uncertainty of measurement U in a normal examination is calculated by U=ku (where k is an inclusion coefficient, for example, 2). The extended uncertainty is calculated similar to $u_{WB}$, $u_{SCS}$, and $u_{QC}$. The extended uncertainty is used in the following description.

Figure 5:
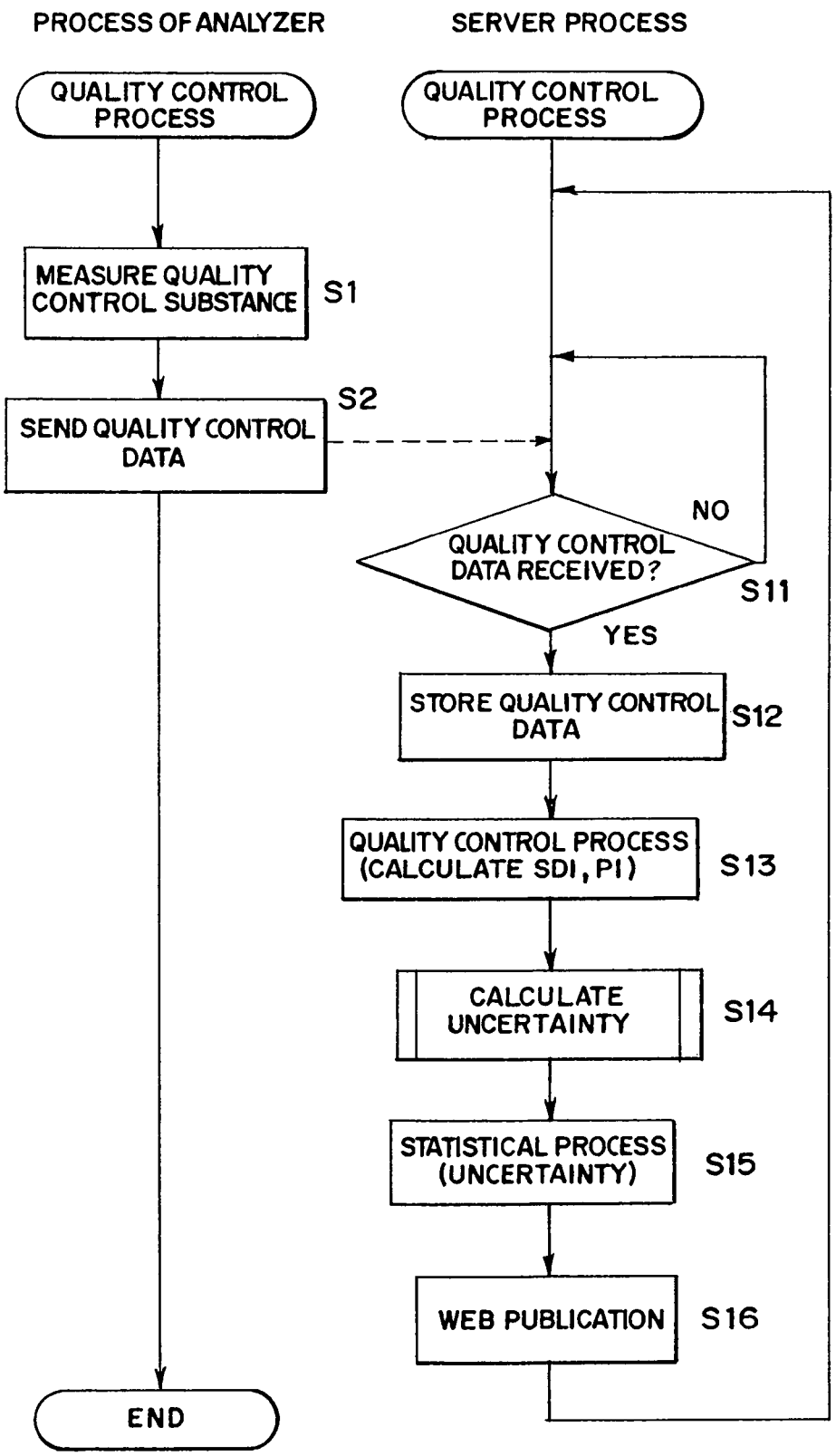
FIG. 5 is a flow chart of the quality control process.

In step S15 of FIG. 5, the server 1 performs quality control (statistical processing) using all uncertainties of measurement U sent from a plurality of analyzers 3 connected to the server 1. This statistical processing may also average the uncertainty of measurement U sent from a plurality of analyzers 3 within a predetermined period, and may determine the standard deviation of the uncertainty of measurement U sent within a predetermined period.

In step S16, the server 1 publishes processing results which include SDI, PI, uncertainty of measurement U of in a normal examination, and quality control results of the uncertainty of measurement U on the WEB (World Wide Web). The processing results published on the WEB are output to the display 4a and the like of the analyzer 3 when the data processing device 4 of the analyzer A or another computer installed at the laboratory starts a WEB browser application program such as Internet Explorer (registered trademark) or the like and accesses a predetermined address and enters a predetermined password. The server 1 may also publish the uncertainty of measurement U obtained by the server 1 for the analyzers 3 other than the analyzer A together with the processing results on the WEB. SDI, PI, and the uncertainty of measurement U may also be calculated for each measurement item and published on the WEB.

The processing results need not necessarily be published on the WEB, inasmuch as the processing results may be sent to the analyzer A. The analyzer 3 which has received the processing results then displays a screen including these results on the display 4a of the analyzer A.

Figure 8:
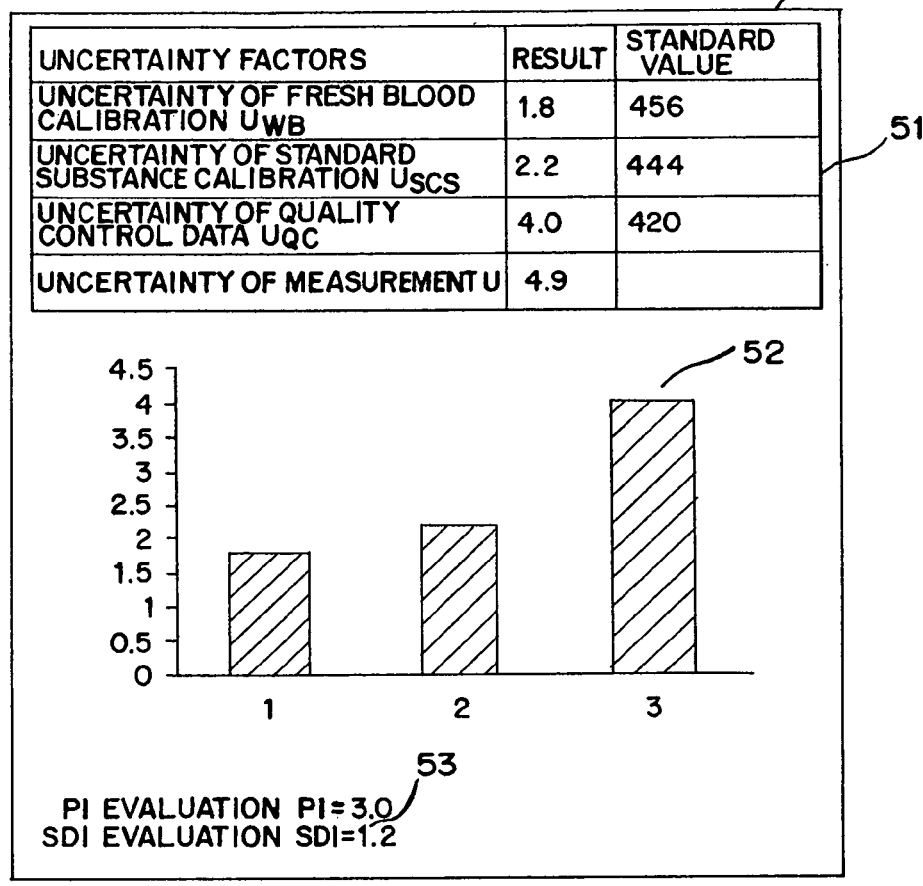
FIG. 8 is an example of a screen displayed on the display of an analyzer.

FIG. 8 shows an example of a screen published on the WEB in step S16. The screen 50 shows the quality control results for red blood cell count. At the top of screen 50 is an uncertainty display region 51. The previously mentioned fresh blood uncertainty of calibration $U_{WB}$, standard substance uncertainty of calibration $U_{SCS}$, quality control data uncertainty $U_{QC}$, and the uncertainty of measurement U value expressing the overall composite result are displayed in the uncertainty display region 51. Furthermore, the standard values of the uncertainty of fresh blood calibration $U_{WB}$, uncertainty of standard substance calibration $U_{SCS}$, and uncertainty of quality control data $U_{QC}$ are also displayed in the uncertainty display region 51.

Graphs 52 are displayed in the center area of the screen 50 to compare the uncertainty of fresh blood calibration $U_{WB}$, uncertainty of standard substance calibration $U_{SCS}$, and uncertainty of quality control data $U_{QC}$. Although the analyzer A does not participate in the calculation of the uncertainty of fresh blood calibration $U_{WB}$ as described above, an undesirable condition in the analyzer A is indicated when the ratio of the uncertainty of standard substance calibration $U_{SCS}$ and uncertainty of quality control data $U_{QC}$ are large compared to the ratio of the uncertainty of fresh blood calibration $U_{WB}$ since the analyzer A does participate in the calculations of the uncertainty of standard substance calibration $U_{SCS}$ and uncertainty of quality control data $U_{QC}$. Therefore, the user of the analyzer A can estimate the status of the analyzer A via the display of graphs. Furthermore, if the data are saved on the server 1, the operator of the server 1 can estimate the status of the analyzer A without visiting the laboratory. The graphs 52 may be relative graphs showing only size comparisons of $U_{WB}$, $U_{SCS}$, and $U_{QC}$, or may also show standard values representing standard uncertainty as comparison values.

A display region 53 showing PI and SDI quality control results is provided at the bottom of the screen 50. The user of the analyzer A can comprehend the status of the analyzer A and determine whether or not a sample is measurable more accurately than the conventional art based on the size of PI and SDI, the size of the uncertainty of measurement U, and the size of t ratio of the uncertainty of standard substance calibration $U_{SCS}$ and the uncertainty of quality control data $U_{QC}$. For example, PI is an advantageous in an overall evaluation of measurement and can be used as an indicator representing the condition of internal quality control in each laboratory. That is, when PI=1, the daily fluctuations of measurement data in the installation (analyzer) is average, such that daily fluctuations are less than average when PI<1, and daily fluctuations are greater than average when PI>1.

Figure 9:
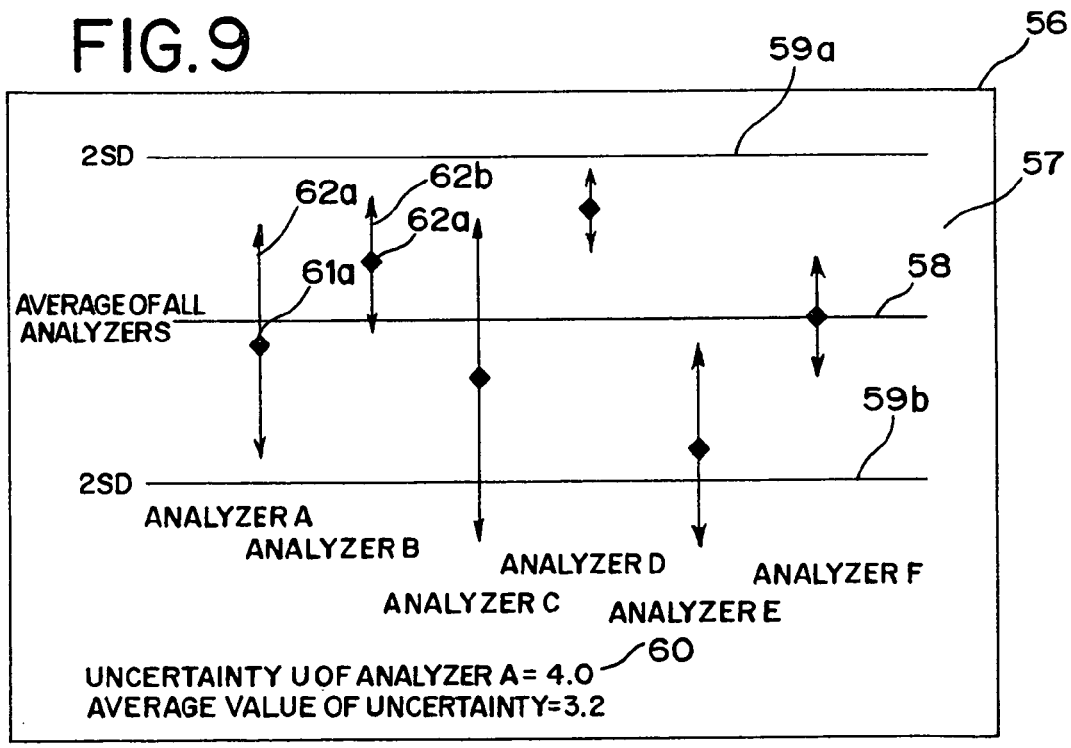
FIG. 9 is an example of a screen displayed on the display of an analyzer.

FIG. 9 shows another example of a screen displayed on the display 4a of the analyzer A in step S4.

The screen 56 shown in FIG. 9 shows a graph 57 that represents the relationship between the quality control data obtained by the predetermined plurality of analyzers 3, and the average values of the quality control data sent from all analyzers 3 connected to the server 1 within a predetermined period. The graph 57 shows line 58 which represents the average values of the quality control data sent from all analyzers 3 connected to the server 1 within a predetermined period, and lines 59a and 59b that represent the standard deviation 2SD. The standard deviation 2SD is only an example, and standard deviations 1SD and 3SD are optionally user settable by the operator of the analyzer A. In graph 57, the diamond points 61a represent the quality control data by the analyzer A, and the arrows 62a represent the uncertainty of measurement of a normal examination by the analyzer A. Similarly, the diamond point 62a represents the quality control data of analyzer B (this analyzer may be another analyzer 3 in the same laboratory, or may be an analyzer 3 installed in another laboratory), and the arrow 62b represents the uncertainty of measurement of the analyzer B. Analyzers C through F are identical. According to the graph 57, the analyzer A has an uncertainty of measurement that is slightly higher than the other analyzer, and the quality control data approach an average value, from which it is understood that the condition of the analyzer is good.

The analyzer B has an uncertainty of measurement that is extremely low compared to other analyzers, and the condition of the analyzer is excellent since the quality control data approach the average value. Although the quality control data of the analyzer C approaches the average value, the uncertainty of measurement is high and there is a possibility the 2SD may be exceeded considering this uncertainty of measurement. Therefore, it is understood that inspection and recalibration of the analyzer C is desirable. The quality control data of the analyzer D somewhat exceed the average value, however the uncertainty of measurement is extremely low and is not considered to exceed the 2SD; therefore it is understood that the condition of the analyzer is good. The quality control data of the analyzer E deviate from the average value, and since there is a possibility the 2SD may be exceeded considering the uncertainty of measurement, it is understood to be desirable to inspect and recalibrate the analyzer. Since the quality control data of the analyzer F are very close to the average value and the uncertainty of measurement is quite low, the condition of the machine is understood to be excellent. Thus, the operator of the analyzer A can determine the status of the analyzer more accurately than the conventional art based on the information which is not obtained in the external quality control of the conventional art.

The screen 56 is also provided with an uncertainty display region 60. The uncertainty display region 60 shows the uncertainty of measurement U in a normal examination by the analyzer A, and the average value of the uncertainty of measurement of the analyzers 3 calculated by the server 1 in step S15 (FIG. 5). Thus, the operator of the analyzer A can compare the uncertainty of measurement U of the analyzer A with the average value of uncertainty, and easily determine the status of the analyzer A.

Although the server 1, calculates the SDI and PI as values for evaluating a single analyzer A in the above embodiment, the present invention is not limited to this configuration inasmuch as SDI and PI may also be calculated to evaluate a plurality of analyzers 3 using the same control substance and installed in the same laboratory. In this instance, the average values of the quality control data obtained by a plurality of analyzers 3 installed in the same laboratory may be substituted for the quality control data of the analyzer A used by the server 1 in step S13.

Although the plurality of analyzers 3 are installed in a plurality of laboratories in the above embodiment, the plurality of analyzers 3 may also be installed in the same laboratory. In this instance, the quality control process may also be performed using only the plurality of analyzers 3 in the same laboratory.

Figure 10:
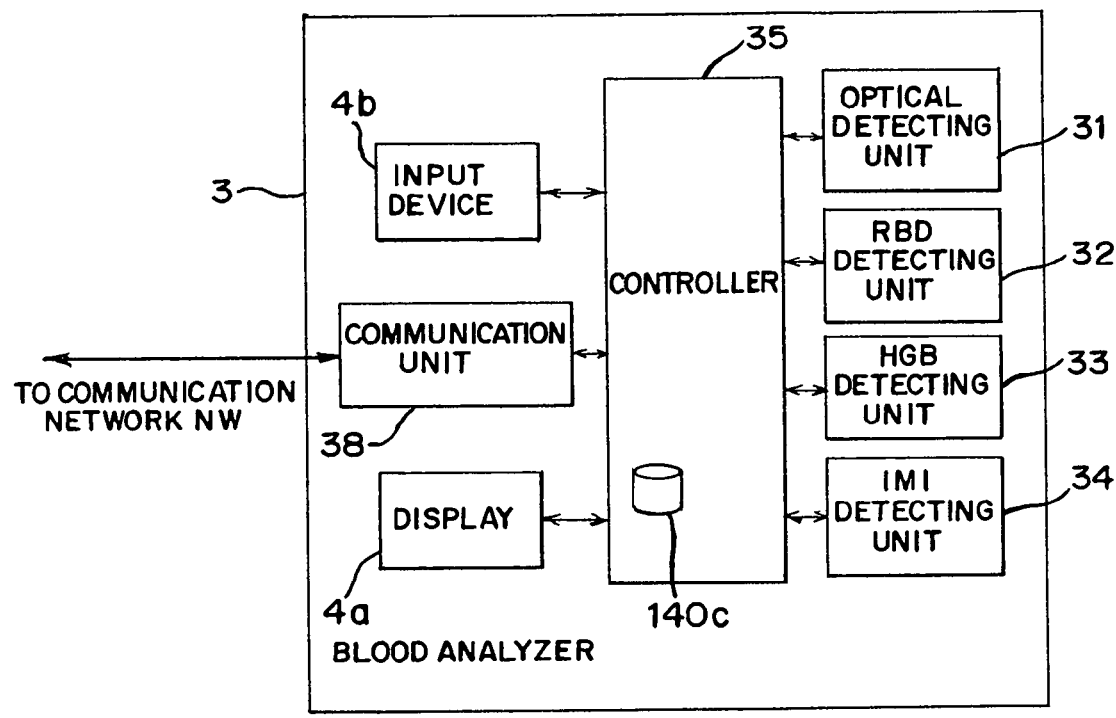
FIG. 10 is a block diagram showing the structure of a modification of the analyzer 3.
Figure 11:
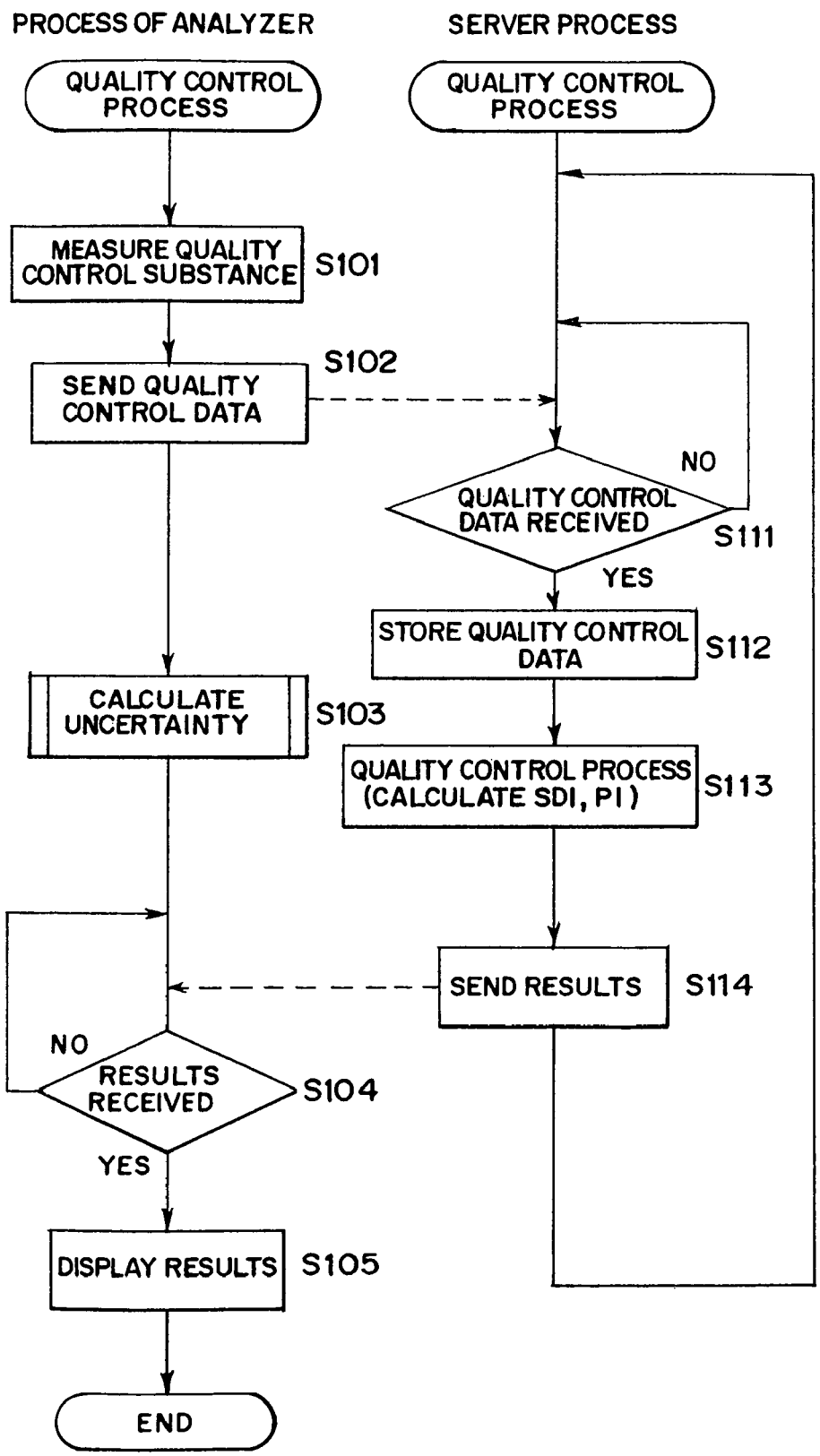
FIG. 11 is a flow chart of a modification of the quality control process.

A modification of the embodiment is described below using FIGS. 10 and 11. In this example, the overall structure of the quality control system 10 is similar to the example shown in FIG. 1, however, the controller 35 of the analyzer A is provided with the calibration uncertainty DB 140c mentioned above.

The quality control process of the modified embodiment is described below with reference to FIG. 11. When the analyzer A measures a quality control substance (step S101), the obtained quality control data are sent to the server 1 (step S102). The server 1 receives the quality control data (step S111), and stores the received quality control data in the quality control DB 104b (step S112). The, the server 1 performs the previously described quality control process based on the quality control data received from a plurality of analyzers 3 (step S113), and sends the results of quality control to the analyzer A (step S114). The analyzer A calculates the uncertainty of measurement U of the analyzer A based on the quality control data obtained in step S101, and the uncertainty of calibration $U_{CAL}$ of the analyzer A stored in the calibration uncertainty DB 140c (step S103). Then, the analyzer A receives the results of quality control from the server 1 (step S104), and displays on the display 4a the screen 50 (refer to FIG. 8) which includes the result of quality control and the uncertainty of measurement U obtained in step S103. In this modification, the server may also publish the result of the quality control on the WEB in step S14.

Although the analyzer 3 receives the result of the quality control from the server 1 in this modification, the server 3 of this modification may also be configured so as to not receive the result of quality control from the server 1. Since the analyzer 3 outputs an uncertainty of measurement only by measuring a quality control substance, the operator can know the uncertainty of measurement simply by normally performing an internal quality control without the necessity of measuring a sample (unknown sample) a plurality of times as per the conventional art.

Although the uncertainty of calibration $U_{CAL}$ is stored beforehand in the calibration uncertainty DB 140c in all the above embodiments, the operator of the quality control server 1 or the analyzer 3 may also prompted to input of the uncertainty of calibration $U_{CAL}$ during the calculation of uncertainty (step S14 or step S103), and store the input uncertainty of calibration $U_{CAL}$ in the calibration uncertainty DB 140c.

What is claimed is:

1. A quality control system comprising a plurality of analyzers and a control device connected to the analyzers via a network, the quality control system comprising:
    measurement units for measuring samples, each of the measurement units being provided in each of the analyzers, respectively;
    quality control data transmitters for transmitting, to the control device via the network, quality control data obtained by the measurement units by measuring quality control samples, each of the quality control data transmitters being provided in each of the analyzers, respectively;
    a quality control data receiver for receiving a plurality of quality control data transmitted from each of the quality control data transmitters, the quality control data receiver being provided in the control device;
    a memory for storing the plurality of quality control data received by the quality control data receiver and a calibration uncertainty of each of the analyzers, wherein each calibration uncertainty reflects a first standard deviation of multiple measurement data obtained by each analyzer by measuring a standard substance multiple times, respectively; and
    a quality control processor provided in the control device and configured for performing operations comprising:
    when the quality control data receiver has received a quality control data from one analyzer among the plurality of analyzers, implementing a quality control of the one analyzer by calculating at least a second standard deviation of multiple quality control data including the plurality of quality control data of the one analyzer stored in the memory and the received quality control data;
    reading out, from the memory, the calibration uncertainty of the one analyzer;
    obtaining a measurement uncertainty of the one analyzer based on a value expressed below:

$$\sqrt{(U_{CAL}^2 + U_{QC}^2)}$$

where $U_{CAL}$ represents the calibration uncertaint of the one analyzer, $U_{QC}$ represents the second standard deviation; and
    generating a report which includes a result of the quality control of the one analyzer and the measurement uncertainty of the one analyzer.

2. The quality control system of claim 1, wherein
    the memory is provided in the control device;
    the control device comprises a report providing unit for providing the report on the WEB; and
    each of the analyzers comprises a web browser for browsing the report provided on the WEB.

3. The quality control system of claim 2, wherein the quality control processor is configured for performing an operation of implementing a statistical processing using a plurality of measurement uncertainties of the plurality of analyzers.

4. The quality control system of claim 1, wherein the quality control processor performs the operation of obtaining the measurement uncertainty by multiplying the value $\sqrt{(U_{CAL}^2 + U_{QC}^2)}$ by a predetermined value.

5. The quality control system of claim 1, wherein the calibration uncertainty is calculated using a standard deviation obtained by measuring an unknown sample whose measurement data are unknown by a first standard analyzer and a standard deviation by measuring the unknown sample by a second standard analyzer.

6. The quality control system of claim 1, wherein
the result of the quality control comprises a result representing a gap between the quality control data obtained by the one analyzer and the quality control data transmitted from each of the analyzers via the network.

7. The quality control system of claim 6, wherein the quality control processor is configured for performing an operation of calculating the result of the quality control based on the equation below:

the result of the quality control=$\{$(quality control data obtained by a predetermined analyzer)−(average value of quality control data within a predetermined time of a plurality of analyzers)$\}/\sqrt{\{1/(m-1)\Sigma(i=1 \text{ to } m)ni(ai-b)^2\}}$ where m represents the number of the plurality of analyzers, ni represents the number of quality control data of each analyzer within a predetermined time, ai represents the average value of the control data of each analyzer within a predetermined time, and b represents the average value of the quality control data of the plurality of analyzers within a predetermined time.

8. The quality control system of claim 1, wherein the result of the quality control includes a result expressing a ratio of a dispersion among the quality control data obtained from the one analyzer during a predetermined period, and a dispersion among the quality control data sent from the plurality of analyzers during a predetermined period.

9. The quality control system of claim 8, wherein the quality control processor is configured for performing an operation of calculating the result of the quality control based on equation below:

the result of the quality control=(standard deviation of quality control data obtained by a predetermined analyzer within a predetermined period)/$\sqrt{\{1/(N-m)\Sigma(i=1 \text{ to } m)(ni-1)Si^2\}}$ where N represents the number of quality control data of a plurality of analyzers within a predetermined period, m represents the number of the plurality of analyzers, ni represents the number of quality control data of each analyzer within a predetermined time, and Si represents the standard deviation of the quality control data of each analyzer within a predetermined time.

10. The quality control system of claim 1, wherein the quality control data comprises numbers of blood cells.

11. The quality control system of claim 1, further comprising
a display unit for displaying the report generated by the quality control processor.

* * * * *

UNITED STATES PATENT AND TRADEMARK OFFICE
CERTIFICATE OF CORRECTION

PATENT NO. : 7,925,461 B2  
APPLICATION NO. : 11/903364  
DATED : April 12, 2011  
INVENTOR(S) : Tadayuki Yamaguchi et al.

Page 1 of 1

It is certified that error appears in the above-identified patent and that said Letters Patent is hereby corrected as shown below:

On the Title Page

In the left column, after item (65), insert a new item as follows.

-- (30)     Foreign Application Priority Data

September 22, 2006     (JP)     2006-256702 --

Signed and Sealed this  
Ninth Day of August, 2011

David J. Kappos  
*Director of the United States Patent and Trademark Office*